(12) United States Patent
Li et al.

(10) Patent No.: US 11,931,389 B2
(45) Date of Patent: Mar. 19, 2024

(54) TABLET OF SPORODERM-REMOVED GANODERMA LUCIDUM SPORE AND PREPARATION METHOD THEREOF

(71) Applicants: Zhejiang Shouxiangu Pharmaceutical Company, Ltd., Zhejiang (CN); Jinhua Shouxiangu Pharmaceutical Co. Ltd, Zhejiang (CN)

(72) Inventors: Zhenhao Li, Zheijiang (CN); Mingyan Li, Zhejiang (CN); Ying Wang, Zhejiang (CN); Huaxian Zheng, Zhejiang (CN); Jing Xu, Zhejiang (CN)

(73) Assignees: Zhejiang Shouxiangu Pharmaceutical Company, Ltd., Jinhua (CN); Jinhua Shouxiangu Pharmaceutical Co. Ltd, Jinhua (CN)

( * ) Notice: Subject to any disclaimer, the term of this patent is extended or adjusted under 35 U.S.C. 154(b) by 70 days.

(21) Appl. No.: 16/478,565

(22) PCT Filed: Feb. 6, 2018

(86) PCT No.: PCT/CN2018/075411
§ 371 (c)(1),
(2) Date: Jul. 17, 2019

(87) PCT Pub. No.: WO2018/188408
PCT Pub. Date: Oct. 18, 2018

(65) Prior Publication Data
US 2019/0343906 A1    Nov. 14, 2019

(30) Foreign Application Priority Data
Apr. 10, 2017   (CN) .......................... 201710227616.6

(51) Int. Cl.
*A61K 36/074* (2006.01)
*A61K 9/20* (2006.01)
*A61P 35/00* (2006.01)

(52) U.S. Cl.
CPC .......... *A61K 36/074* (2013.01); *A61K 9/2018* (2013.01); *A61K 9/2027* (2013.01); *A61K 9/2095* (2013.01); *A61P 35/00* (2018.01); *A61K 2236/331* (2013.01); *A61K 2236/39* (2013.01); *A61K 2236/51* (2013.01)

(58) Field of Classification Search
CPC .................................................. A61K 36/074
See application file for complete search history.

(56) References Cited

U.S. PATENT DOCUMENTS
2016/0317594 A1    11/2016   Huang et al.

FOREIGN PATENT DOCUMENTS

| CN | 101091727 A | | 12/2007 | |
|---|---|---|---|---|
| CN | 101731622 A | | 6/2010 | |
| CN | 103006728 A | | 4/2013 | |
| CN | 103550264 A | * | 2/2014 | |
| CN | 104013652 A | * | 9/2014 | |
| CN | 104069366 A | | 10/2014 | |
| CN | 104857045 A | | 8/2015 | |
| CN | 104873624 A | | 9/2015 | |
| CN | 104013652 A | | 5/2017 | |
| CN | 107115304 A | | 9/2017 | |
| CN | 105106250 A | | 7/2019 | |
| FI | 111605 B | * | 8/2003 | |
| KR | 20160040213 A | * | 4/2016 | ......... A61K 47/6951 |

OTHER PUBLICATIONS

PCT International Preliminary Report on Patentability, Xiaofan Tang, dated Oct. 15, 2019 (Year: 2019).*
KR-20160040213-A translated doc (Year: 2016).*
CN-103550264-A translated doc (Year: 2014).*
CN-104013652-A translated doc (Year: 2013).*
Rojas (Screening of several excipients for direct compression of tablets: A new perspective based on functional properties, Rev Cienc Farm Basica Apl., 2013; 34(10:17-23) (Year: 2013).*
Wang et. al. (Anticarcinogenic effects of water extract of sporoderm-broken spores of Ganoderma lucidum on colorectal cancer in vitro and in vivo, International Journal of Oncology 50: 1541-1554, 2017) (Year: 2017).*
FI111605B translated doc (Year: 2003).*
Benito-Roman (β-Glucan recovery from Ganoderma lucidum by means of pressurized hot water and supercritical CO2, Food and Bioproducts Processing, vol. 98, Apr. 21-28, 2016). (Year: 2016).*
https://unacademy.com/content/nta-ugc/study-material/pharmaceutical-analysis/what-is-the-effect-of-temperature-and-ph-on-extraction/). (Year: 2023).*
Ginseng Research, China Academic Journal Electronic Publishing House, Apr. 17, 2017 (http://www.cnki.net).

(Continued)

*Primary Examiner* — Terry A McKelvey
*Assistant Examiner* — Jacob A Boeckelman

(57) ABSTRACT

The present invention provides a tablet of sporoderm-removed *Ganoderma lucidum* spore, which includes the following raw materials by weight parts: 13-20 parts of an aqueous extract of sporoderm-disrupted *Ganoderma lucidum* spore powder, 3-5 parts of sorbitol, and 0.8-1.2 parts of povidone K30; A method for preparing the tablet of sporoderm-removed *Ganoderma lucidum* spore includes the following steps: mixing the aqueous extract of sporoderm-disrupted *Ganoderma lucidum* spore powder, sorbitol and povidone K30 for 10-30 min, and subjecting the obtained mixture to granulating, screening and drying to obtain a granular material; and tableting the granular material to obtain the tablet of sporoderm-removed *Ganoderma lucidum* spore. The tablet of sporoderm-removed *Ganoderma lucidum* spore has a much higher content of active components, which are also easier to be absorbed. The tablet of sporoderm-removed *Ganoderma lucidum* spore is of effectively enhancing the body immunity and have anti-radiation and anti-tumor effects; and the dosage form of the tablet is convenient to carry and take.

4 Claims, 5 Drawing Sheets

(56) References Cited

OTHER PUBLICATIONS

Zeng Xiangyun et al., Development of Liaodong Bencao brand Ganoderma lucidum spore powder tablets, Liaoning Xiangyun Pharmaceutical Jilin Ginseng Research Institute, 5 pages.

Su-Lan Sun, Experimental research of glossy ganoderma pills on antifatigue effect, The Medicine Development Center of Sun Yet-sen University, Guangzhou 510080, China, 2 pages.

Hong-Yan Liu et al., Determination of total flavones in *Vitex trifolia* L. var. simplicifolia Cham. in Shandong, Shandong University of Traditional Chinese Medicine, Jinan 250014, China; 2. The Second People's Hospital of Taian, Taian 271021, China, 1 page.

\* cited by examiner

TABLET OF SPORODERM-REMOVED GANODERMA LUCIDUM SPORE AND PREPARATION METHOD THEREOF

CROSS-REFERENCE TO RELATED APPLICATIONS

This application is a US National Phase of International Patent Application PCT/CN2018/075411 filed Feb. 6, 2018, which claims priority to Chinese Patent Application No. 201710227616.6 filed to the State Intellectual Property Office on Apr. 10, 2017 and entitled "TABLET OF SPORODERM-REMOVED *GANODERMA LUCIDUM* SPORE AND PREPARATION METHOD THEREOF", which is incorporated herein by reference in its entirety.

TECHNICAL FIELD

The present invention relates to the technical field of healthcare foods, and more particular to a tablet of sporoderm-removed *Ganoderma lucidum* spore and a preparation method thereof.

BACKGROUND

Human's understanding of health has been further deepened with the development of science and technology. It has been stated by medical experts of the World Health Organization from more than 50 countries that, the best treatment for diseases is prevention. At present, examinations in the hospitals can only diagnose diseases that have already occurred. Once the disease is confirmed, it is often too late to cure the disease even with the best means in modern medicine. In a famous ancient Chinese medical text "The Inner Canon of Huangdi", it has been stated "superior treat before sick, prevention is better than treatment". Superior treat before sick means taking appropriate measures to prevent occurrence and development of a disease, and is a main idea of traditional Chinese medicine. For any disease, the incidence of the disease would be very low, and even completely avoided, as long as prevention of disease and body maintenance are conducted first.

*Ganoderma lucidum* spores are extremely tiny ovoid germ cells that are ejected from the gills of the fruiting body at its mature period, which is considered as the "seed" of this fungus. It condenses the essence of *Ganoderma lucidum*, and is rich in a variety of biologically active substances such as polysaccharides, triterpenoids, proteins, polypeptides, amino acids, nucleosides, organic germanium, trace elements and vitamins. *Ganoderma lucidum* spore has various activities such as enhancing immunity, resisting radiation and scavenging free radicals, with few side effects. However, *Ganoderma lucidum* spore has a hard sporoderm which is mainly composed of chitin and cellulose, thus is hard to be fully absorbed in the body. In order to improve the absorption of *Ganoderma lucidum* spore, the sporoderm is generally crushed by grinding or milling method. However, after sporoderm-breaking, the fragments of sporoderm is still in the spore powder, and the mass fractions of active constituents are still very low.

SUMMARY

In view of the above, an objective of the present invention is to provide a tablet of sporoderm-removed *Ganoderma lucidum* spore, which is easy to absorb, is capable of effectively improving the immunity, preventing and treating radiation diseases (especially those caused by radiation of a 60Co-γ ray), cancers (especially gastric cancer, lymphoma, and lung adenocarcinoma), and is convenient to carry and take.

To achieve the above objective, the present invention provides the following technical solutions:

The present invention provides a tablet of sporoderm-removed *Ganoderma lucidum* spore, including the following raw materials by weight parts: 13-20 parts of sporoderm-disrupted *Ganoderma lucidum* spore powder, 3-5 parts of sorbitol, and 0.8-1.2 parts of povidone K30; in the tablet of sporoderm-removed *Ganoderma lucidum* spore, the mass fraction of total polysaccharides is 1.5-7.6%, and the mass fraction of total triterpenes content is 0.9-4%; and the sporoderm-disrupted *Ganoderma lucidum* spore powder is used to prepare an aqueous extract of the sporoderm-disrupted *Ganoderma lucidum* spore powder (namely the sporoderm-removed *Ganoderma lucidum* spore powder), which is prepared by water extraction, concentration, drying and pulverization of the sporoderm-disrupted *Ganoderma lucidum* spore powder.

Preferably, the particle size of the aqueous extract of sporoderm-disrupted *Ganoderma lucidum* spore powder is less than 0.180 mm.

Preferably, the yield of the aqueous extract of sporoderm-disrupted *Ganoderma lucidum* spore powder is 15-25%.

Preferably, the mass of a single tablet of sporoderm-removed *Ganoderma lucidum* spore is 0.8-0.9 g.

The present invention further provides a method for preparing the above-described tablet of sporoderm-removed *Ganoderma lucidum* spore, including the following steps:

1) mixing the aqueous extract of sporoderm-disrupted *Ganoderma lucidum* spore powder, sorbitol and povidone K30 for 10-30 min, and subjecting the obtained mixture to granulating, screening and drying to obtain a granular material; and 2) tableting the granular material obtained in step 1) to obtain the tablet of sporoderm-removed *Ganoderma lucidum* spore.

Preferably, the sieving mesh is 14-16 mesh during the granulation process, and the sieving mesh is 18-20 mesh during the screening process.

Preferably, the aqueous extract of sporoderm-disrupted *Ganoderma lucidum* spore powder is obtained by water extraction, concentration, drying and pulverization of the sporoderm-disrupted *Ganoderma lucidum* spore powder.

Preferably, the water extraction includes three stages, where the temperature of first-stage water extraction is 25-30° C., the time of the first-stage water extraction is 1-3 h, and the mass of water used for the first-stage water extraction is 10-15 times than that of the sporoderm-disrupted *Ganoderma lucidum* spore powder; and the temperature of second-stage water extraction and third-stage water extraction is 95-100° C., the time of the second-stage water extraction and the third-stage water extraction is independently 1-3 h, and the masses of water used for the second-stage water extraction and the third-stage water extraction are independently 8-12 times than that of the sporoderm-disrupted *Ganoderma lucidum* spore powder.

Preferably, the vacuum degree of the concentration is −0.07 to −0.09 Mpa, and the temperature of the concentration is 60-70° C.

Preferably, the drying is microwave drying, the vacuum degree of the microwave drying is −0.08 Mpa, and the temperature of the microwave drying is 60-70° C.

The present invention further provides use of the above-described tablet of sporoderm-removed *Ganoderma lucidum* spore in cancer prevention and treatment.

Preferably, the cancer includes gastric cancer, lymphoma, and lung adenocarcinoma.

The present invention further provides use of the above-described tablet of sporoderm-removed *Ganoderma lucidum* spore in prevention and treatment of radiation-induced diseases.

Preferably, the radiation-induced diseases include diseases caused by 60Co-γ ray irradiation.

The tablet of sporoderm-removed *Ganoderma lucidum* spore provided by the present invention includes 13-20 parts of sporoderm-disrupted *Ganoderma lucidum* spore powder, 3-5 parts of sorbitol, and 0.8-1.2 parts of povidone K30; in the tablet of sporoderm-removed *Ganoderma lucidum* spore, the total polysaccharides content is 1.5-7.6% and the total triterpenes content is 0.9-4%, and thus the tablet has higher contents of active constituents than conventional *Ganoderma lucidum* spore product, making the active components easy to be absorbed, and capable of effectively enhancing the immunity; and have anti-radiation and anti-tumor effects. The tablet dosage form makes it convenient to take.

DETAILED DESCRIPTION

Figure 1:
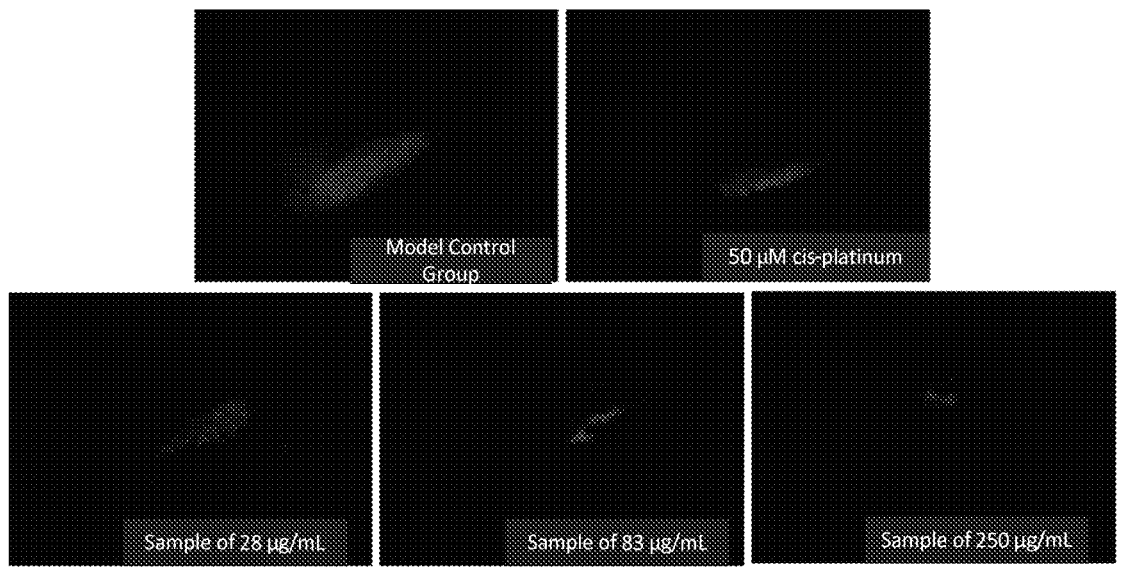
FIG. 1 shows the phenogram of zebrafish treated with the tablet of sporoderm-removed *Ganoderma lucidum* spore after transplant with human gastric carcinoma tumor (SGC-7901)

The present invention is further described below with reference to the accompanying embodiments.

The present invention provides a tablet of sporoderm-removed *Ganoderma lucidum* spore, which includes the following raw materials by weight parts: 13-20 parts of sporoderm-disrupted *Ganoderma lucidum* spore powder, 3-5 parts of sorbitol, and 0.8-1.2 parts of povidone K30; in the tablet of sporoderm-removed *Ganoderma lucidum* spore, the total polysaccharides content is 1.5-7.6% and the total triterpenes content is 0.9-4%; and the sporoderm-disrupted *Ganoderma lucidum* spore powder is used to prepare an aqueous extract of the sporoderm-disrupted *Ganoderma lucidum* spore powder (namely the sporoderm-removed *Ganoderma lucidum* spore powder), which is prepared by water extraction, concentration, drying and pulverization of the sporoderm-disrupted *Ganoderma lucidum* spore powder.

The tablet of sporoderm-removed *Ganoderma lucidum* spore provided by the present invention includes 13-20 parts, preferably 14-18 parts, and more preferably 15-17 parts of the sporoderm-disrupted *Ganoderma lucidum* spore powder. In the present invention, the particle size of the aqueous extract of sporoderm-disrupted *Ganoderma lucidum* spore powder is preferably less than 0.180 mm, and more preferably 0.100-0.160 mm.

In the present invention, the aqueous extract of sporoderm-disrupted *Ganoderma lucidum* spore powder is the main active ingredient of the tablet, which contains total polysaccharides and total triterpenes. The aqueous extract of sporoderm-disrupted *Ganoderma lucidum* spore powder is preferably obtained by conducting water extraction of the sporoderm-disrupted *Ganoderma lucidum* spore powder, and the yield of the aqueous extract of sporoderm-disrupted *Ganoderma lucidum* spore powder is preferably 15-25%, and more preferably 18-22%. The sporoderm of the *Ganoderma lucidum* spore has two layers of hard wall shell accounting for about 60% of the mass of the entire spore, which is mainly composed of chitin. The sporoderm is acid- and alkali-resistant, and is difficult to be absorbed and utilized in the human body. In the present invention, after the sporoderm-disrupted *Ganoderma lucidum* spore powder is extracted by water, the sporoderm can be removed by extraction and filtration, so the product is free of the sporoderm, and the contents of the active components such as total polysaccharides and total triterpenes are greatly improved. In the aqueous extract of sporoderm-disrupted *Ganoderma lucidum* spore powder, the total polysaccharides content is 2-10 g/100 g, and preferably 4-8 g/100 g, and the total triterpenes content is 1.2-5 g/100 g, and preferably 3-4.5 g/100 g. Compared with the sporoderm-disrupted *Ganoderma lucidum* spore powder, the aqueous extract of the sporoderm-disrupted *Ganoderma lucidum* spore powder does not contain sporoderm residues, so the contents of the active components total polysaccharides and total triterpenes are increased by 8-12 times. The active components of the tablet of sporoderm-removed *Ganoderma lucidum* spore are therefore easier to absorb, thereby effectively enhancing the activities. For the active components contained in the tablet of sporoderm-removed *Ganoderma lucidum* spore provided by the present invention, the total polysaccharides content is preferably 1.5-7.6%, and more preferably 3-7%; and the total triterpenes content is preferably 0.9-4%, and more preferably 2-3.5%.

Based on the mass of the sporoderm-disrupted *Ganoderma lucidum* spore powder, the tablet of sporoderm-removed *Ganoderma lucidum* spore provided by the present invention includes 3-5 parts, and preferably 4 parts of sorbitol. In the present invention, sorbitol acts as a moisturizer and sweetener of the tablet, which maintains the moisture in the tablet, and improves the taste of the tablet.

Based on the mass of the sporoderm-disrupted *Ganoderma lucidum* spore powder, the tablet of sporoderm-removed *Ganoderma lucidum* spore provided by the present invention includes 0.8-1.2 parts, and preferably 0.9-1.1 parts of povidone K30. In the present invention, povidone K30 acts as a binder of the tablet, so that the individual components of the tablet are bonded together to facilitate molding.

The present invention also provides the preparing method of the tablet of sporoderm-removed *Ganoderma lucidum* spore described in the above technical solution, including the following steps:

1) mixing the aqueous extract of the sporoderm-disrupted *Ganoderma lucidum* spore powder, sorbitol and povidone K30 for 10-30 min, and subjecting the obtained mixture to granulating, screening and drying to obtain a granular material; and 2) tableting the granular material obtained in step 1) to obtain the tablet of sporoderm-removed *Ganoderma lucidum* spore.

In the present invention, preferably the aqueous extract of the sporoderm-disrupted *Ganoderma lucidum* spore powder is obtained by conducting water extraction, concentration, drying and pulverization of the sporoderm-disrupted *Ganoderma lucidum* spore powder. In the present invention, the water extraction includes three stages, where in particularly is: mixing the sporoderm-disrupted *Ganoderma lucidum* spore powder with water and subjecting the mixture to the first-stage water extraction; mixing the residues obtained in the first stage with water and subjecting the mixture to the second-stage water extraction; and mixing the residues obtained from the second stage with water and subjecting the mixture to the third-stage water extraction, and combining the liquids obtained from the three-stage water extraction to obtain an extract solution. In the present invention, the temperature of the first-stage water extraction is preferably 25-30° C., and more preferably 26-28° C., and the time of the first-stage water extraction is preferably 1-3 h, and more preferably 2 h; during the water extraction, the mass of water used for the first-stage water extraction is preferably 10-15 times, and more preferably 12-14 times than that of the sporoderm-disrupted *Ganoderma lucidum* spore powder. In the present invention, the first-stage extraction liquid is collected after the completion of the first-stage water extraction; the present invention has no particular limitation on the collecting method, and any collecting method conventional in the art may be used, and specifically in the embodiments of the present invention a method of filtration or centrifugation can be adopted to collect a extracting solution and remove the shell wall of the *Ganoderma lucidum* spore.

In the present invention, the second-stage water extraction is conducted after the first-stage extraction liquid is collected, where the mass of water used for the second-stage water extraction is preferably 8-12 times, and more preferably 9-11 times of the mass of sporoderm-disrupted *Ganoderma lucidum* spore powder; the temperature of the second-stage water extraction is preferably 95-100° C., and more preferably 97-99° C.; and the time of the second-stage water extraction is preferably 1-3 h, and more preferably 2 h. In the present invention, the second-stage extraction liquid is collected after the completion of the second-stage water extraction.

In the present invention, the third-stage water extraction is conducted after the second-stage extraction liquid is collected, where the mass of water used for the third-stage water extraction is preferably 8-12 times, and more preferably 9-11 times of the mass of sporoderm-disrupted *Ganoderma lucidum* spore powder; the temperature of the third-stage water extraction is preferably 95-100° C., and more preferably 97-99° C.; and the time of the third-stage water extraction is preferably 1-3 h, and more preferably 2 h. In the present invention, the third-stage extraction liquid is collected after the completion of the third-stage water extraction.

In the present invention, after completion of the three-stage water extraction, the first-stage aqueous extract solution, the second-stage aqueous extract solution and the third-stage aqueous extract solution are combined together to obtain an aqueous extract solution; and the combined aqueous extract solution is concentrated to obtain a concentrated solution. In the present invention, the concentration is preferably performed under reduced pressure; the vacuum degree of the concentration is preferably −0.07 to −0.09 Mpa, and more preferably −0.08 Mpa; the temperature of the concentration under reduced pressure is preferably 60-70 C°, more preferably 62-68 C°, and most preferably 65 C°; and the density after the concentration under reduced pressure is preferably 1.05-1.15, more preferably 1.08-1.12, and most preferably 1.10.

In the present invention, after the concentrated solution is obtained, the concentrated solution is dried to obtain a dry extract. In the present invention, the drying is preferably conducted by microwave drying; the vacuum degree of the microwave drying is preferably −0.08 Mpa; and the temperature of the microwave drying is preferably 60-70 C°, more preferably 63-68 C°, and most preferably 65 C°.

In the present invention, after the dry extract is obtained, preferably the dry extract is pulverized to obtain the aqueous extract of the sporoderm-disrupted *Ganoderma lucidum* spore powder. The pulverization described in the present invention may be carried out by a conventional pulverization method in the art, and in particular in an embodiment of the present invention. Pulverization is conducted by using a pulverizer, and then sieving is conducted and the undersized components are collected; during the pulverization, the sieving mesh is preferably 60-100 mesh, and more preferably 80 mesh. The yield of the aqueous extract of the sporoderm-disrupted *Ganoderma lucidum* spore powder is preferably 15-25%, more preferably 18-22%, and most preferably 20%.

In the present invention, after the aqueous extract of the sporoderm-disrupted *Ganoderma lucidum* spore powder is obtained, the aqueous extract of the sporoderm-disrupted *Ganoderma lucidum* spore powder is mixed with sorbitol and povidone K30 to obtain a mixed material. The mixing method described in the present invention is conducted by using a powder mixing method conventional in the art, and specifically in the embodiments of the present invention a method of mixing under stirring is used, where the mixing time is preferably 10-30 min, and more preferably 15-25 min.

In the present invention, after the mixed material is obtained, the mixed material is subjected to granulating, sieving and drying to obtain a granular material; the present invention has no particular limitation on the granulating, screening and drying, and a granulating, screening and drying technical solution conventional in the art may be employed; in the present invention, the sieving mesh is preferably 14-16 mesh during the granulation process, and the sieving mesh is preferably 18-20 mesh during the screening process; and the drying is carried out as long as a granular material capable of effectively forming a tablet can be obtained.

In the present invention, after the granular material is obtained, the granular material is tableted to obtain the tablet of sporoderm-removed *Ganoderma lucidum* spore. The present invention has no other special requirements on the tableting method, and a tableting method conventional in the art may be used. In the present invention, the mass of a single tablet of sporoderm-removed *Ganoderma lucidum* spore is preferably 0.8-0.9 g, and more preferably 0.85 g.

The tablet of sporoderm-removed *Ganoderma lucidum* spore of the present invention can be used as a health care product, and in particular when used, the tablet is administrated two times a day, and 3 tablets each time, depending on the physical state of the people who take it.

The tablet of sporoderm-removed *Ganoderma lucidum* spore and the preparation method thereof as provided by the present invention will be described in detail in connection with the following embodiments, but they should not be construed as limiting the claimed scope of the present invention.

Embodiment 1

The raw materials of the tablet of sporoderm-removed *Ganoderma lucidum* spore included 16.5 parts of sporoderm-disrupted *Ganoderma lucidum* spore powder, 4.2 parts of sorbitol, and 1 part of povidone K30.

An aqueous extract of sporoderm-disrupted *Ganoderma lucidum* spore powder was obtained by conducting water extraction, concentration, drying and pulverization on the sporoderm-disrupted *Ganoderma lucidum* spore powder. The temperature of the first-stage water extraction was preferably 27° C., the time of the first-stage water extraction was preferably 2 h, and the mass of water used for the first-stage water extraction was preferably 12 times than that of the sporoderm-disrupted *Ganoderma lucidum* spore powder; in the present invention, the first-stage extraction liquid was collected after the completion of the first-stage water extraction; and the mass of water used for the second-stage water extraction was preferably 10 times than that of the sporoderm-disrupted *Ganoderma lucidum* spore powder, the temperature of the second-stage water extraction was 99° C., the time of the second-stage water extraction was 2 h. In the present invention, the second-stage extraction liquid was collected after the completion of the second-stage water extraction. The mass of water used for the third-stage water extraction was preferably 11 times than that of the sporoderm-disrupted *Ganoderma lucidum* spore powder; the temperature of the third-stage water extraction was 98° C.; and the time of the third-stage water extraction was 2 h. The sporoderm of the *Ganoderma lucidum* spore is removed through centrifugation and the extracting solution is collected. The first-stage aqueous extract solution, the second-stage aqueous extract solution and the third-stage aqueous extract solution were combined and then concentrated under reduced pressure, where the vacuum degree of the concentration was −0.09 MPa, the temperature of the concentration under reduced pressure was 65° C., and the density after the concentration under reduced pressure was 1.10.

Microwave drying was conducted after the concentration, where the vacuum degree was −0.08 Mpa, and the temperature was 65° C. After the drying, pulverization was carried out to obtain the aqueous extract of sporoderm-disrupted *Ganoderma lucidum* spore powder; and the sieving mesh during the pulverization was 80 mesh. 4.125 parts by weight of the aqueous extract of sporoderm-disrupted *Ganoderma lucidum* spore powder was obtained after the pulverization, and the yield of the aqueous extract of sporoderm-disrupted *Ganoderma lucidum* spore powder was 25%.

In the present invention, after the aqueous extract of sporoderm-disrupted *Ganoderma lucidum* spore powder was obtained, it was mixed with sorbitol and povidone K30 for 20 min to obtain a mixed material, and the mixed material was subjected to granulating of 14 mesh, screening of 20 mesh, and drying to obtain a granular material; the granular material was tableted to obtain the tablet of sporoderm-removed *Ganoderma lucidum* spore, where the mass of a single tablet of sporoderm-removed *Ganoderma lucidum* spore was 0.85 g. For the tablet of sporoderm-removed *Ganoderma lucidum* spore, the total polysaccharides content was 2.8%, and the total triterpenes content was 1.38%, such that the extraction rate of the sporoderm-removed *Ganoderma lucidum* spore powder was much higher than that of conventional sporoderm-disrupted *Ganoderma lucidum* spore powder in the market.

Embodiment 2

The raw materials of the tablet of sporoderm-removed *Ganoderma lucidum* spore included 18 parts of sporoderm-disrupted *Ganoderma lucidum* spore powder, 4 parts of sorbitol, and 0.9 part of povidone K30.

An aqueous extract of sporoderm-disrupted *Ganoderma lucidum* spore powder was obtained by conducting water extraction, concentration, drying and pulverization on the sporoderm-disrupted *Ganoderma lucidum* spore powder. The temperature of the first-stage water extraction was preferably 26° C., the time of the first-stage water extraction was preferably 2 h, and the mass of water used for the first-stage water extraction was preferably 13 times than that of the sporoderm-disrupted *Ganoderma lucidum* spore powder; in the present invention, the first-stage extraction liquid was collected after the completion of the first-stage water extraction; and the mass of water used for the second-stage water extraction was preferably 9.5 times than that of the sporoderm-disrupted *Ganoderma lucidum* spore powder, where the temperature of the second-stage water extraction was 99° C., and the time of the second-stage water extraction was 2 h. In the present invention, the second-stage extraction liquid was collected after the completion of the second-stage water extraction. The mass of water used for the third-stage water extraction was preferably 10 times than that of the sporoderm-disrupted *Ganoderma lucidum* spore powder; the temperature of the third-stage water extraction was 98° C.; and the time of the third-stage water extraction was 2 h. The sporoderm of the *Ganoderma lucidum* spore is removed through centrifugation and the extracting solution is collected. The first-stage aqueous extract solution, the second-stage aqueous extract solution and the third-stage aqueous extract solution were combined and then concentrated under reduced pressure, where the vacuum degree of the concentration was-0.08 MPa, the temperature of the concentration under reduced pressure was 65° C., and the density after the concentration under reduced pressure was 1.11.

Microwave drying was conducted after the concentration, where the vacuum degree was −0.07 Mpa, and the temperature was 65 C°. After the drying, pulverization was carried out to obtain the aqueous extract of sporoderm-disrupted *Ganoderma lucidum* spore powder; the sieving mesh during the pulverization was 80 mesh. 3.6 parts by weight of the aqueous extract of sporoderm-disrupted *Ganoderma lucidum* spore powder was obtained after the pulverization, and the yield was as 20%.

In the present invention, after the aqueous extract of sporoderm-disrupted *Ganoderma lucidum* spore powder was obtained, the aqueous extract of sporoderm-disrupted *Ganoderma lucidum* spore powder was mixed with sorbitol and povidone K30 for 25 min to obtain a mixed material, and the mixed material was subjected to granulating of 14 mesh, screening of 20 mesh, and drying to obtain a granular material; the granular material were tableted to obtain the tablet of sporoderm-removed *Ganoderma lucidum* spore, where the mass of a single tablet of sporoderm-removed *Ganoderma lucidum* spore was 0.85 g. For the tablet of sporoderm-removed *Ganoderma lucidum* spore, the total polysaccharides content was 2.76%, and the total triterpenes content was 1.43%, such that the extraction rate of the sporoderm-removed *Ganoderma lucidum* spore powder was much higher than that of conventional sporoderm-disrupted *Ganoderma lucidum* spore powder in the market.

Embodiment 3

Efficacy and toxicity tests of the tablet of sporoderm-removed *Ganoderma lucidum* spore The tablet of sporoderm-removed *Ganoderma lucidum* spore powder obtained in Embodiment 1 was tested in terms of efficacy and toxicity by the following experiments.

Auxiliary protection function to the radiation test was carried out according to the "Technical Specification for Health Food Inspection and Evaluation" (2003 edition). The tablet sample was administered to mice at doses of 1.00 g/kg·bw/d for 20 consecutive days. After irradiation with 60Co γ-Rays, four indicators, including the number of white blood cells, the number of bone marrow nucleated cells (Table 1), the activity of superoxide dismutase (SOD) in liver tissues, and the half hemolysis concentration (HC50) of serum were evaluated. The results showed that the numbers of both white blood cells and bone marrow nucleated cells were significantly higher in the embodiment 1 group compared to the control group after irradiation. These results indicated that the sample had an auxiliary protection function to the radiation hazard.

TABLE 1

Result of Bone-marrow nucleated cell experiment

| Groups | Number of Animals | Number of hemolysis plaques (number/$10^6$ spleen cells) | Count of bone-marrow nucleated cells ($10^7$/ml) |
|---|---|---|---|
| Negative Control Group | 10 | 95 ± 28 | 1.47 ± 0.31 |
| Embodiment 1 | 10 | 132 ± 23 | 2.01 ± 0.45 |

Immuno-enhancement test was carried out according to the "Technical Specification for Health Food Inspection and Evaluation" (2003 edition). Mice were orally administered for 1 month with 0.17 g/kg·bw/d, 0.33 g/kg·bw/d, or 1.00 g/kg·bw/d tablet of sporoderm-removed *Ganoderma lucidum* spores, after which the cellular immune response, humoral immune response, monocyte-macrophage function, and NK cell activity were examined. The four indicators were all improved at the dosage of 1.00 g/kg, indicating the sample had immune-enhancing effects under the tested condition.

Acute toxicity test: the cute toxicity test was carried out according to the "Technical Specifications for Health Food Inspection and Evaluation" (2003 edition), where the acute oral MTD of female and male mice was greater than 20,000 mg/kg·bw, indicating the sample belonged to a non-toxic level according to the acute toxicity dose classification standard.

Micronucleus test: the micronucleus test was carried out according to the "Technical Specification for Health Food Inspection and Evaluation" (2003 edition), where 3 dose groups of 2.5, 5.0, 10.0 g/kg·bw were set, and the mice were intragastrically administered. The micronucleus test result of the sample was negative.

Sperm malformation test: the sperm malformation test was carried out according to the "Technical Specification for Health Food Inspection and Evaluation" (2003 edition), where 3 dose groups of 2.5, 5.0, 10.0 g/kg·bw were set, and the male mice were intragastrically administered. The sperm malformation test result of the sample was negative.

Ames test: the Ames test was carried out according to the "Technical Specification for Health Food Inspection and Evaluation" (2003 edition), where a plate incorporation method was adopted, and the test doses were respectively of 5,000, 1,000, 200, 40 and 8 μg/dish. The Ames test result of the sample was negative.

30 days feeding test in rats: the 30 days feeding test in rats was carried out according to the "Technical Specification for Health Food Inspection and Evaluation" (2003 edition), where for female rats, 3 dose groups of 4.06, 2.63, 1.18 g/kg·bw/d (equivalent to 122 times, 79 times, and 35 times of the amount recommended for human body) were set; and for male rats, 3 dose groups of 3.79, 2.45, 1.13 g/kg·bw/d (equivalent to 114 times, 74 times, and 34 times of the amount recommended for human body) were set. The experimental results showed that no harmful effect of the tablet of sporoderm-removed *Ganoderma lucidum* spores was observed from the tested indicators of all the dose groups in the 30 days feeding test in rats.

It can be seen from the above tests that the tablet of sporoderm-removed *Ganoderma lucidum* spores is safe and non-toxic, and have immuno-enhancement and anti-radiation functions. Because the contents of active constituents are relatively high with total polysaccharides content ranges from 1.5% to 7.6%, and the total triterpenes content ranges 0.9% to 4%, the effects of tablet of sporoderm-removed *Ganoderma lucidum* spores are good.

Embodiment 4

Efficacy Tests of the Tablet of Sporoderm-Removed *Ganoderma lucidum* Spore on Zebrafishes Experimental Animal 1. Wild type AB strain zebrafishes were bred in a natural paired mating mode. A total of 330 zebrafishes were used for the anti-gastric cancer experiment with the age of 2 days after fertilization. Each group contained 30 zebrafishes.

2. Wild type AB strain zebrafishes were bred in a natural paired mating mode. A total of 480 zebrafishes were used for the anti-lung cancer experiment with the age of 2 days after fertilization. Each group contained 30 zebrafishes.

3. Wild type AB strain zebrafishes were bred in a natural paired mating mode. A total of 660 zebrafishes were used for the anti-lymphatic cancer experiment with the age of 2 days after fertilization. Each group contained 30 zebrafishes.

The zebrafishes were fed in fish-farming water (water quality: 200 mg of instant sea salt was added per 1 L reverse osmosis water, with a conductivity of 480-510 μS/cm; pH of 6.9-7.2; hardness of 53.7-71.6 mg/L $CaCO_3$) at 28 C. T° he experimental animal license number is: SYXK (Zhejiang) 2012-0171. The feeding management met the requirements of international AAALAC certification Test Drugs The sample of sporoderm-removed *Ganoderma lucidum* spore powder, i.e., the aqueous extract of sporoderm-disrupted *Ganoderma lucidum* spore powder, was dissolved in ultrapure water before use. The batch number was 16042301, which was provided by Zhejiang Shouxiangu Pharmaceutical Co. Ltd on 10 May 2016.

Vincristine sulfate, which was white powder of LOT#K1306055, purchased from Aladdin, and stored in a cool cabinet. Before use, it was dissolved with dimethyl sulfoxide (DMSO) into a 5 mM stock solution, and the final working solution had a DMSO concentration of 0.1%.

Cis-platinum, which was yellow powder of LOT#K1520124, purchased from Aladdin, and stored in a cool cabinet. Before use, it was dissolved with dimethyl sulfoxide (DMSO) into a 50 mM stock solution, and the final working solution had a DMSO concentration of 0.1%.

Instruments and Reagents

An electronic focusing continuously zoom fluorescence microscope (AZ100, Nikon); a dissecting microscope (SZX7, OLYMPUS, Japan); a camera attached to a microscope (TK-C1481EC); a precision electronic balance (CP214, Ohaus); a 6-well Plate (Nest Biotech); methylcellulose (Aladdin, Shanghai, China).

Experiment 1. Anti-Gastric Cancer Effects of Tablet of Sporoderm-Removed *Ganoderma lucidum* Spore on Zebrafish 1 Concentration Groups Experimental group 1 model control group Experimental group 2 positive control drug of 50 μM cis-platinum Experimental group 3 sample of 28 μg/mL Experimental group 4 sample of 83 μg/mL Experimental group 5 sample of 250 μg/mL Concentration determination 2 The maximum tolerated concentration (MTC) of each sample at 35 C° was determined at 250 μg/mL; and according to the project scheme, the sample concentrations for anti-gastric cancer were set as: 28 μg/mL (1/9 MTC), 83 μg/mL (1/3 MTC) and 250 μg/mL (MTC).

3 Model Establishment

Human gastric cancer (SGC-7901) cells were labeled with a red fluorescent dye (CM-Dil), and transplanted into zebrafish yolk sacs by microinjection, with about 200 cells being transplanted per zebrafish, so as to establish the zebrafish human gastric cancer transplanted tumor model.

4 Experimental Method 4.1 Determination of Maximum Tolerated Concentration (MTC)

The wild-type AB strain zebrafishes were randomly selected into the 6-well plate, and were treated with water-dissolved samples at concentrations respectively of 10, 100, 250, 500, 1,000, and 2000 μg/mL, respectively and meanwhile a normal control group was set. During treatment with the test sample, the dead zebrafishes were counted and removed every day; after the zebrafishes were treated with the test sample for 2 days, the movement states and death conditions of the zebrafishes were observed to determine the MTC of the test sample on the zebrafish.

4.2 Evaluation of Anti-Gastric Cancer Effect of the Sample

Human gastric cancer (SGC-7901) cells were labeled with CM-Dil, and transplanted into 2 dpf wild type AB strain zebrafish yolk sacs by microinjection, with about 200 cells per zebrafish, so as to establish a zebrafish human gastric cancer (SGC-7901) transplanted model; and the zebrafishes injected with the SGC-7901 cells were fed at 35° C. until 3 dpf.

Zebrafishes with better consistence in transplanted tumor cells were picked out under a microscope, randomly assigned to a 6-well plate, and were given in a water-dissolving administration manner respectively with the samples at concentrations respectively of 28, 83 and 250 μg/mL and the positive control drug cis-platinum at a concentration of 50 μM; and meanwhile a model control group was set, where there were 30 zebrafishes per well, and the volume of each well was 5 mL. The zebrafishes in each group were continually cultured at 35° C., and after 2 days, 10 zebrafishes were randomly selected from each experiment (concentration) group to observe under a fluorescence microscope, and photographs of the 10 zebrafishes were taken and saved; and the photographs were analyzed using Nikon NIS-Elements D 3.10 Advanced image processing software to calculate the fluorescence intensities of cancer cells. The inhibitory effects of samples on the zebrafish gastric cancer (SGC-7901) transplanted tumor were respectively evaluated with the fluorescence intensities, and the tumor inhibition effect was calculated using the following equation.

$$\text{Tumor inhibition effect (\%)} = \left(1 - \frac{S(\text{Test Sample Group})}{S(\text{Model Control Group})}\right) \times 100\%$$

A concentration-effect curve was drawn according to the inhibition effects on the transplanted tumor; statistical analysis was performed by variance analysis and Dunnett's T-test, where $p < 0.05$ was considered as a significant difference.

Note: the wild-type AB strain zebrafish did not produce red fluorescence itself, and after CM-Dil-labeled cells were injected into zebrafish yolk sacs, red fluorescence can be excited at a certain wavelength, where the sum of fluorescence intensities had positive correlation with the number of cancer cells. The larger the sum of the fluorescence intensities was, the larger the number of cancer cells was.

5. Experimental Result 5.1 MTC

According to Table 1, when the sample was in the concentration range of 500 μg/mL to 1,000 μg/mL, death occurred in the zebrafishes; and thus it was determined that the MTC of the sample on the zebrafish is 250 μg/mL, and the experiment concentrations for evaluation were all selected as 28 μg/mL (1/9 MTC), 83 μg/mL (1/3 MTC), and 250 μg/mL (MTC).

TABLE 1

"concentration-mortality" statistical analysis of test samples

| Groups | Sample | |
|---|---|---|
| | Death Count | Mortality (%) |
| Normal Control Group | 0 | 0 |
| 10 μg/mL | 0 | 0 |
| 100 μg/mL | 0 | 0 |
| 250 μg/mL | 0 | 0 |
| 500 μg/mL | 30 | 100 |
| 1000 μg/mL | 30 | 100 |
| 2000 μg/mL | 30 | 100 |

5.2 Evaluation of Anti-Gastric Cancer Effect of the Sample

For the positive control drug cis-platinum at the concentration of 50 μM, the sum of fluorescence intensity values of the zebrafish human gastric cancer (SGC-7901) transplanted tumor cells was 256,812 pixels, p<0.001 as compared with the model control group (408,759 pixels), and the tumor inhibition effect was 37%, indicating that cis-platinum has a significant inhibition effect on the growth of the zebra fish human gastric cancer (SGC-7901) transplanted tumor.

Figure 2:
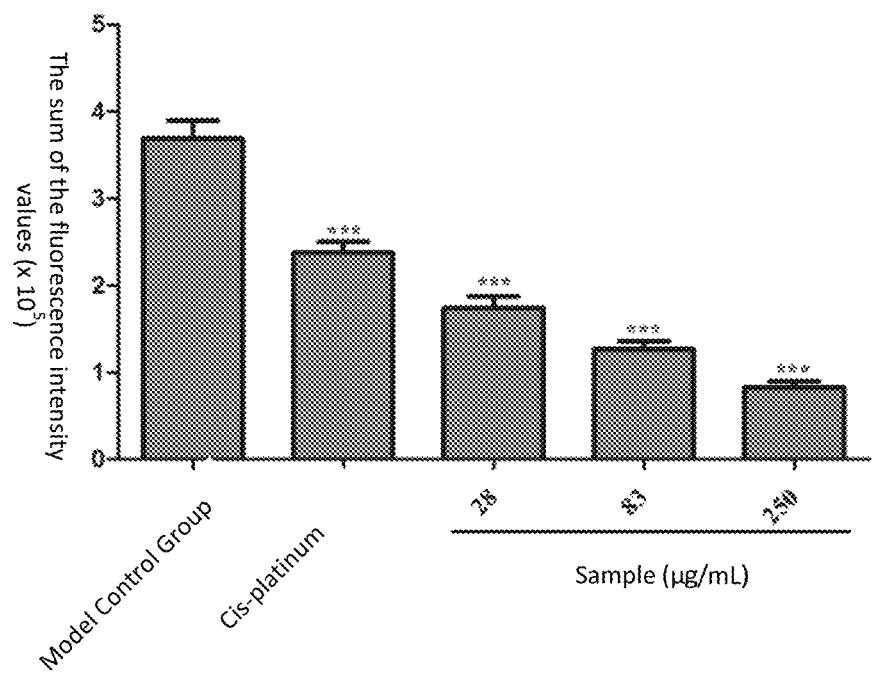
FIG. 2 shows the fluorescence intensity of zebrafish treated with the tablet of sporoderm-removed *Ganoderma lucidum* spore after transplant with human gastric carcinoma tumor (SGC-7901)
Figure 3:
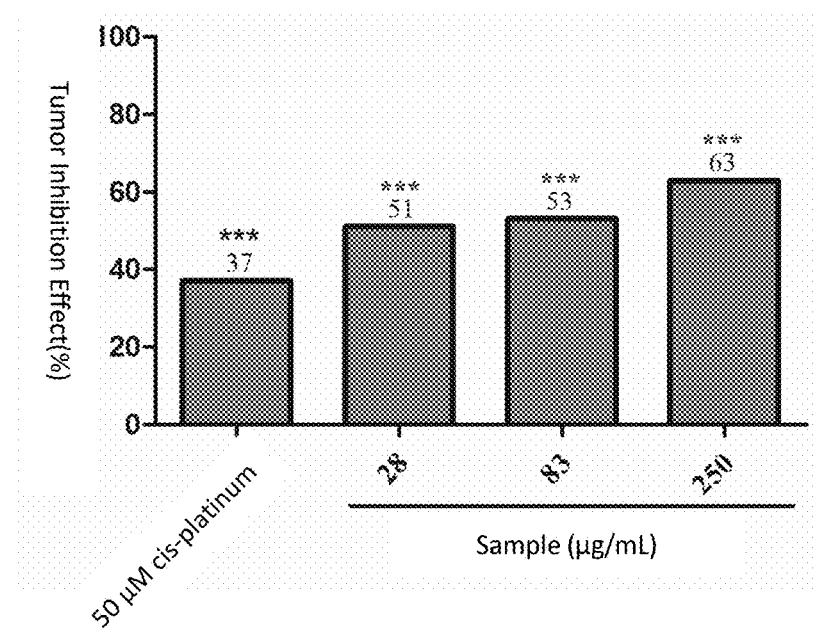
FIG. 3 shows the inhibition effect of the tablet of sporoderm-removed *Ganoderma lucidum* spore on zebrafish transplanted with human gastric carcinoma tumor (SGC-7901)

When the samples are of the concentrations of 28, 83 and 250 μg/mL, the sums of the fluorescence intensity values of the zebrafish human gastric cancer (SGC-7901) transplanted tumor cells were 202,089, 190,268, and 149,865 pixels, respectively, p<0.001 & p<0.001 & p<0.001 compared with the model control group, and the tumor inhibition effects were respectively 51%, 53%, and 63%. See Table 2, FIG. 1, FIG. 2 and FIG. 3 for details.

TABLE 2

Inhibition effect of samples on zebrafish human gastric cancer (SGC-7901) transplanted tumor (n = 10)

| Experimental Groups | Concentration (μg/mL) | Pixel of Sum of Fluorescence Intensities (mean ± SE) | Inhibition Effect (%) |
|---|---|---|---|
| Model Control Group | — | 408759 ± 28052 | — |
| cis-platinum | 50 μM | 256812 ± 12535*** | 37*** |
| Sample | 28 | 202089 ± 21964*** | 51*** |
|  | 83 | 190268 ± 30337*** | 53*** |
|  | 250 | 149865 ± 20737*** | 63*** |

Note:
as compared with the model control group,
*p < 0.05,
***p < 0.001

Experiment 2. Anti-Lymphatic Cancer Effect of the Tablet of Sporoderm-Removed *Ganoderma lucidum* Spore 1. Concentration Groups
Experimental group 1 model control group
Experimental group 2 positive control drug of 5 μM vincristine
Experimental group 3 sample of 1 μg/mL
Experimental group 4 sample of 3 μg/mL
Experimental group 5 sample of 9 μg/mL
2. Concentration determination
It was the same as that of Experiment 1.
3. Model Establishment
Human lymphatic cancer (Ramos) cells were labeled with a red fluorescent dye (CM-Dil), and transplanted into zebrafish yolk sacs by microinjection, with about 200 cells being transplanted per zebrafish, so as to establish a zebrafish human lymphatic cancer transplanted tumor model.
4. Experimental Method
Human lymphatic cancer (Ramos) cells were labeled with CM-Dil, and transplanted into 2 dpf wild type AB strain zebrafish yolk sacs by microinjection, with about 200 cells being transplanted per zebrafish, so as to establish a zebrafish human lymphatic cancer transplanted model; and the zebrafishes injected with the human lymphatic cancer cells were fed at 35° C. until 3 dpf.

Zebrafishes with better consistence in transplanted tumor cells were picked out under a microscope, randomly assigned to a 6-well plate, and were given in a water-dissolving administration manner respectively with the samples at concentrations respectively of 1, 3 and 9 μg/mL and the positive control drug vincristine at a concentration of 5 μM; and meanwhile a model control group was set, where there were 30 zebrafishes per well (concentration group), and the volume of each well was 5 mL. The zebrafishes in each experiment (concentration) group were continually cultured at 35° C., and after 2 days, 10 zebrafishes were randomly selected from each experiment (concentration) group to observe under a fluorescence microscope, and photographs of the 10 zebrafishes were taken and saved; and the photographs were analyzed using Nikon NIS-Elements D 3.10 Advanced image processing software to calculate the fluorescence intensities of cancer cells. The inhibitory effect of the sample on the zebrafish lymphatic cancer (Ramos) transplanted tumor was evaluated with the fluorescence intensities, and the tumor inhibition effect was calculated using the following equation.

$$\text{Tumor inhibition effect (\%)} = \left(1 - \frac{S(\text{Test Sample Group})}{S(\text{Model Control Group})}\right) \times 100\%$$

A concentration-effect curve was drawn according to a growth inhibition effect on the transplanted tumor; statistical analysis was performed by variance analysis and Dunnett's T-test, where p<0.05 was considered as a significant difference; such that a representative experimental map was provided.

Note: the wild-type AB strain zebrafish did not produce red fluorescence itself, and after CM-Dil-labeled cells were injected into zebrafish yolk sacs, red fluorescence can be excited at a certain wavelength, where the sum of fluorescence intensities had positive correlation with the number of cancer cells, and the larger the sum of the fluorescence intensities was, the larger the number of cancer cells was.

5. Experimental Result
For the positive control drug vincristine at the concentration of 5 μM, the fluorescence intensity of the zebrafish human lymphatic cancer (Ramos) transplanted tumor cells was 152,159 pixels, p<0.001 as compared with the model control group (233,644 pixels), and the tumor inhibition effect was 35%, indicating that vincristine has a significant inhibition effect on the growth of the zebra fish human lymphatic cancer (Ramos) transplanted tumor.

Figure 4:
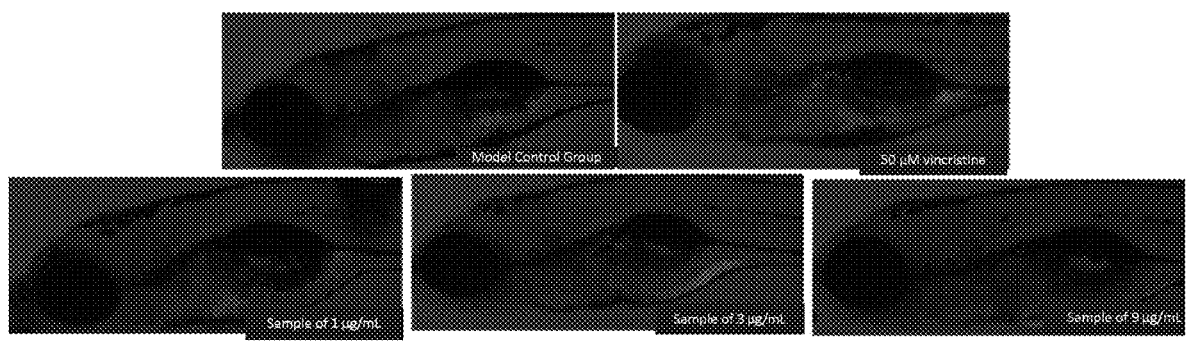
FIG. 4 shows the phenogram of zebrafish treated with the tablet of sporoderm-removed *Ganoderma lucidum* spore after transplant with human lymphatic cancer (Ramos)
Figure 5:
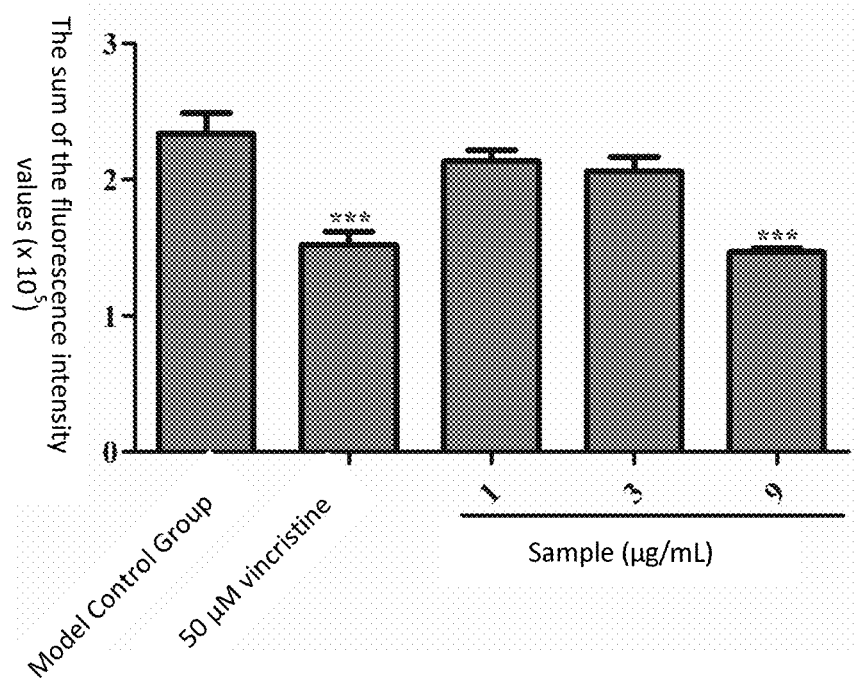
FIG. 5 shows the fluorescence intensity of zebrafish treated with the tablet of sporoderm-removed *Ganoderma lucidum* spore after transplant with human lymphatic cancer (Ramos)
Figure 6:
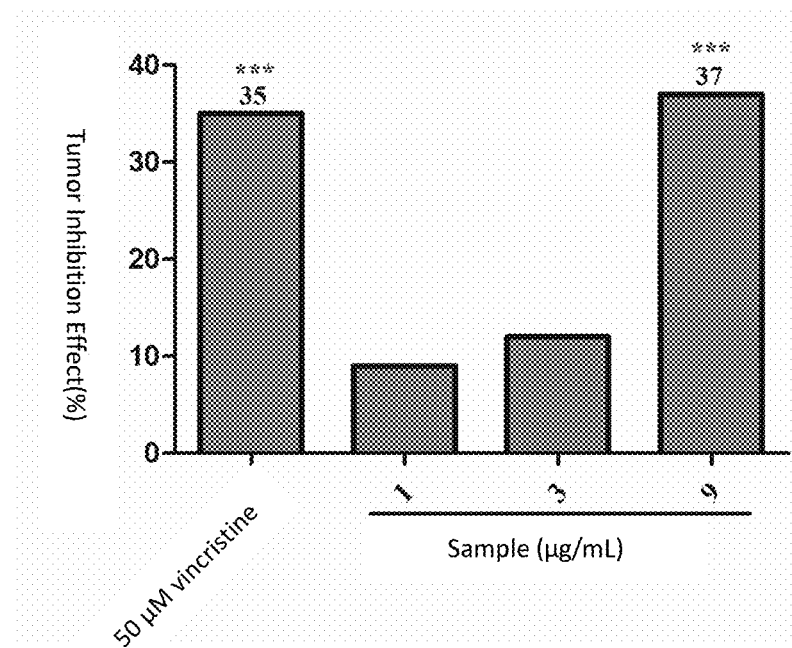
FIG. 6 shows the inhibition effect of the tablet of sporoderm-removed *Ganoderma lucidum* spore on zebrafish transplanted with human lymphatic cancer (Ramos)

When the samples were of the concentrations of 1, 3 and 9 μg/mL, the sums of the fluorescence intensity values of the zebrafish human lymphatic cancer (Ramos) transplanted tumor cells were respectively 213,273, 206,096, and 146,990 pixels, where as compared with the model control group, for the group of 1 μg/mL and the group of 3 μg/mL p>0.05, and the tumor inhibition effects were respectively 9% and 12%; and for the group of 250 ng/mL, p<0.001, and the tumor inhibition effect was 37%. See Table 3, FIG. 4, FIG. 5 and FIG. 6 for details.

TABLE 3

Inhibition effect of the sample sporoderm-removed Ganoderma lucidum spore powder (the aqueous extract of the sporoderm-disrupted Ganoderma lucidum spore powder) on zebrafish human lymphatic cancer (Ramos) transplanted tumor (n = 10)

| Experimental Groups | Concentration (μg/mL) | Pixel of Sum of Fluorescence Intensities (mean ± SE) | Inhibition Effect (%) |
|---|---|---|---|
| Model Control Group | — | 233644 ± 15172 | — |

TABLE 3-continued

Inhibition effect of the sample sporoderm-removed Ganoderma lucidum spore powder (the aqueous extract of the sporoderm-disrupted Ganoderma lucidum spore powder) on zebrafish human lymphatic cancer (Ramos) transplanted tumor (n = 10)

| Experimental Groups | Concentration (μg/mL) | Pixel of Sum of Fluorescence Intensities (mean ± SE) | Inhibition Effect (%) |
|---|---|---|---|
| vincristine | 5 μM | 152159 ± 9682*** | 35*** |
| Sample | 1 | 213273 ± 8249 | 9 |
|  | 3 | 206096 ± 10613 | 12 |
|  | 9 | 146990 ± 2747*** | 37*** |

Note:
as compared with the model control group,
***p < 0.001

Experiment 3. Anti-Lung Cancer Effect of the Tablet of Sporoderm-Removed Ganoderma lucidum Spore 1. Concentration Groups
Experimental group 1 model control group
Experimental group 2 positive control drug of 50 μM cis-platinum
Experimental group 3 sample of 1 μg/mL
Experimental group 4 sample of 3 μg/mL
Experimental group 5 sample of 9 μg/mL 2. Concentration determination
It was the same as that of Experiment 1.

3. Model Establishment
Human lung adenocarcinoma (A549) cells were labeled with a red fluorescent dye (CM-Dil), and transplanted into zebrafish yolk sacs by microinjection, with about 200 cells being transplanted per zebrafish, so as to establish a zebrafish human lung adenocarcinoma transplanted tumor model.

4. Experimental Method
Human lung adenocarcinoma (A549) cells were labeled with CM-Dil, and transplanted into 2 dpf wild type AB strain zebrafish yolk sacs by microinjection, with about 200 cells being transplanted per zebrafish, so as to establish a zebrafish human lung adenocarcinoma (A549) transplanted model; and the zebrafishes injected with the A549 cells were fed at 35° C. until 3 dpf.

Zebrafishes with better consistence in transplanted tumor cells were picked out under a microscope, randomly assigned to a 6-well plate, and were given in a water-dissolving administration manner respectively with the samples at concentrations respectively of 1, 3 and 9 μg/mL and the positive control drug cis-platinum at a concentration of 50 μM; and meanwhile a model control group was set, where there were 30 zebrafishes per well (concentration group), and the volume of each well was 5 mL. The zebrafishes in each experiment (concentration) group were continually cultured at 35° C., and after 2 days, 10 zebrafishes were randomly selected from each experiment (concentration) group to observe under a fluorescence microscope, and photographs of the 10 zebrafishes were taken and saved; and the photographs were analyzed using Nikon NIS-Elements D 3.10 Advanced image processing software to calculate the fluorescence intensities of cancer cells. The inhibitory effect of the sample No. 3 on the zebrafish lung adenocarcinoma (A549) transplanted tumor was evaluated with the fluorescence intensities, and the tumor inhibition effect was calculated using the following equation.

$$\text{Tumor inhibition effect (\%)} = \left(1 - \frac{S(\text{Test Sample Group})}{S(\text{Model Control Group})}\right) \times 100\%$$

A concentration-effect curve was drawn according to the growth inhibition effect on the transplanted tumor; statistical analysis was performed by variance analysis and Dunnett's T-test, where p<0.05 was considered as a significant difference; such that a representative experimental map was provided.

Note:
the wild-type AB strain zebrafish did not produce red fluorescence itself, and after CM-Dil-labeled cells were injected into zebrafish yolk sacs, red fluorescence can be excited at a certain wavelength, where the sum of fluorescence intensities had positive correlation with the number of cancer cells, and the larger the sum of the fluorescence intensities was, the larger the number of cancer cells was.

Experimental Result

For the positive control drug cis-platinum at the concentration of 50 μM, the sum of fluorescence intensity values of the zebrafish human lung adenocarcinoma (A549) transplanted tumor cells was 211,187 pixels, p<0.01 as compared with the model control group (297,891 pixels), and the tumor inhibition effect was 29%, indicating that cis-platinum has a significant inhibition effect on the growth of the zebra fish human lung adenocarcinoma (A549) transplanted tumor.

Figure 7:
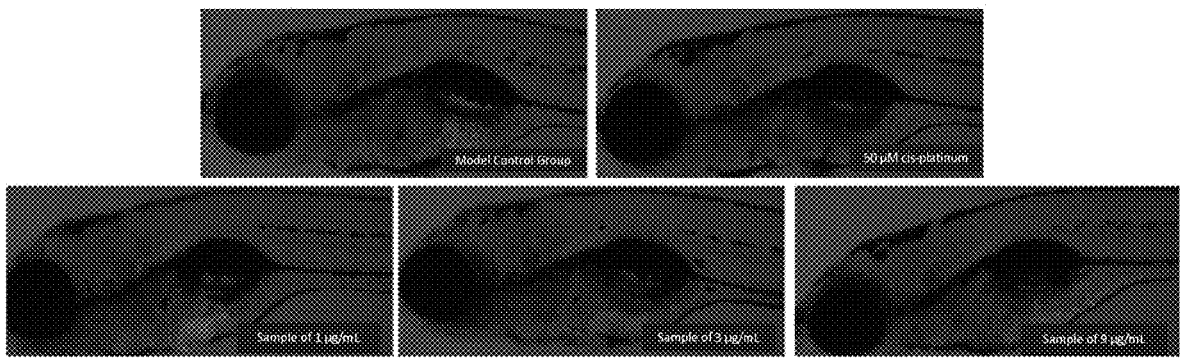
FIG. 7 shows the phenogram of zebrafish treated with the tablet of sporoderm-removed *Ganoderma lucidum* spore after transplant with human lung adenocarcinoma (A549)
Figure 8:
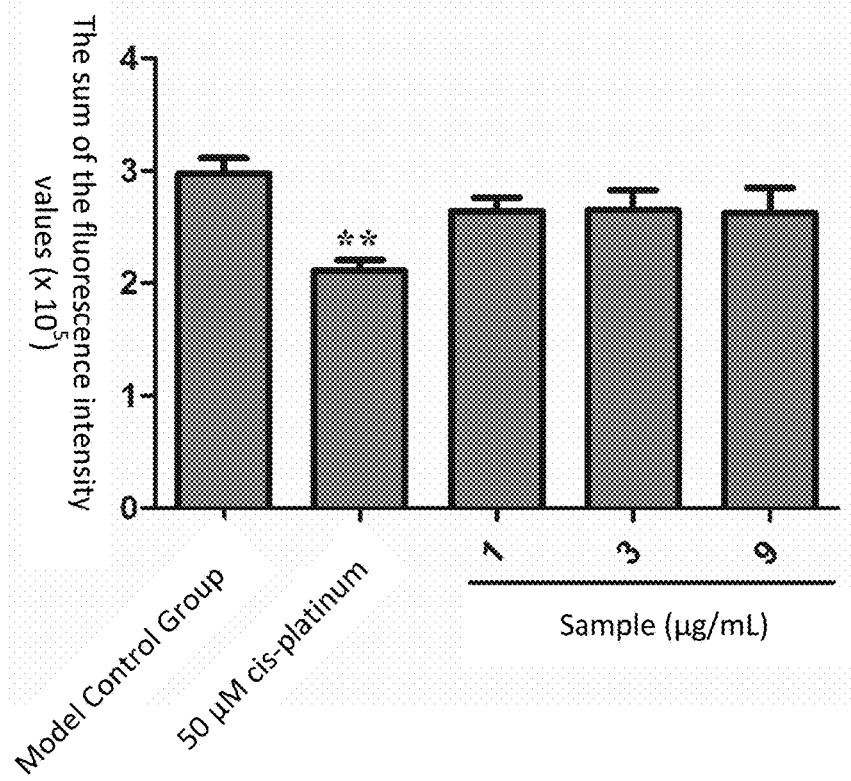
FIG. 8 shows the fluorescence intensity of zebrafish treated with the tablet of sporoderm-removed *Ganoderma lucidum* spore after transplant with human lung adenocarcinoma (A549)
Figure 9:
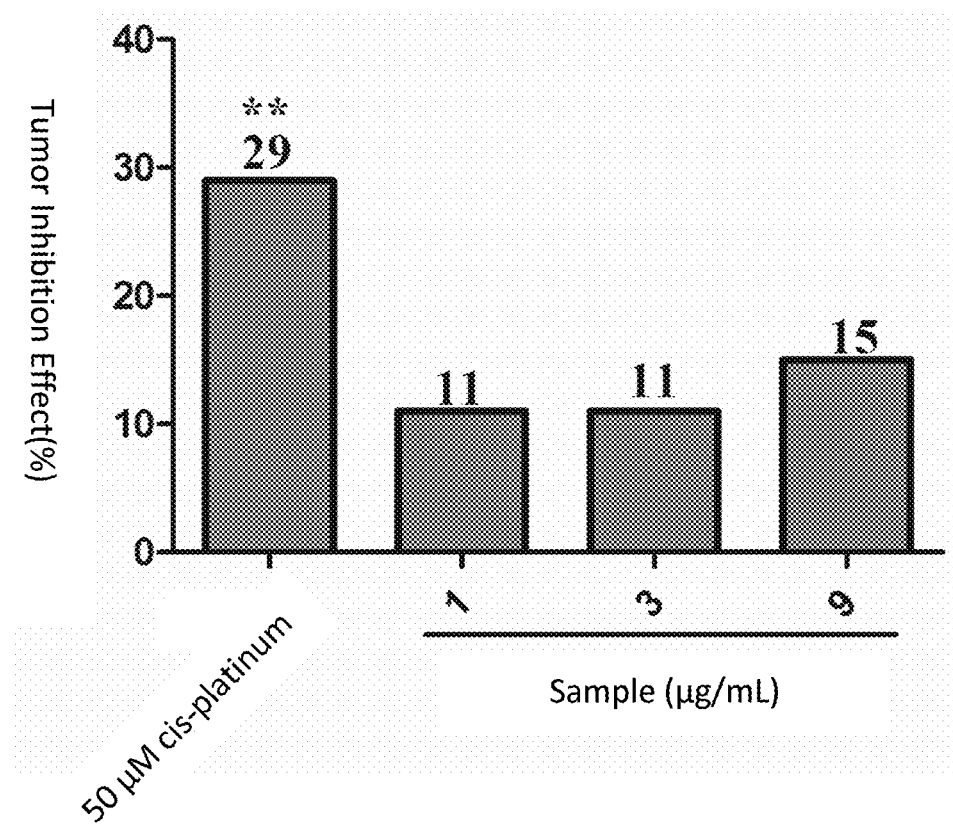
FIG. 9 shows the inhibition effect of the tablet of sporoderm-removed *Ganoderma lucidum* spore on zebrafish transplanted with human lung adenocarcinoma (A549)

When the samples were of the concentrations of 1, 3 and 9 μg/mL, the sums of the fluorescence intensity values of the zebrafish human lung adenocarcinoma (A549) transplanted tumor cells were respectively 264,348, 265,484, and 252,527 pixels, for the 3 concentration groups the average p>0.05 as compared with the model control group, and the tumor inhibition effects were respectively 11%, 11%, and 15%. See Table 4, FIG. 7, FIG. 8 and FIG. 9 for details.

TABLE 4

Inhibition effect of the sample sporoderm-removed Ganoderma lucidum spore powder (the aqueous extract of the sporoderm-disrupted Ganoderma lucidum spore powder) on zebrafish human lung adenocarcinoma (A549) transplanted tumor (n = 10)

| Experimental Groups | Concentration (μg/mL) | Pixel of Sum of Fluorescence Intensities (mean ± SE) | Inhibition Effect (%) |
|---|---|---|---|
| Model Control Group | — | 297891 ± 13681 | — |
| cis-platinum | 50 μM | 211187 ± 9375** | 29** |
| Sample | 28 | 264348 ± 11739 | 11 |
|  | 83 | 265484 ± 17435 | 11 |
|  | 250 | 252527 ± 17064 | 15 |

Note:
as compared with the model control group,
*p < 0.05,
**p < 0.01,
***p < 0.001

The test results showed that: under the condition of this experiment, the tablet of sporoderm-removed Ganoderma lucidum spore of the present invention had inhibitory effects on human gastric cancer tumor, human lung adenocarcinoma, and the human lymphatic cancer transplanted tumor on zebrafish models, where the inhibitory effects on the zebrafish human gastric cancer transplanted tumor and zebrafish human lymphatic cancer transplanted tumor were stronger.

Function test for enhancing the immunity in animal: the test was conducted according to the "Technical Specification for Health Food Inspection and Evaluation" (2003 edition), where mice were orally administrated for one month with the test doses of 3 dose groups respectively being 0.17, 0.33, and 1.00 g/kg·bw/d. The cellular immune function, humoral immune function, monocyte-macrophage function and cell viability of NK cells of the mice were determined. The results showed that, the group of 1.00 g/kg·bw/d had a higher difference between the absorbance with the addition of a ConA hole and the absorbance without the addition of the ConA hole, and a higher ear-pinna weight gain than those of the group of 0 g/kg·bw/d; the group of 1.00 g/kg·bw/d had a higher number of mouse hemolytic plaques and a higher mouse-serum half hemolytic value ($HC_{50}$) than those of the group of 0 g/kg·bw/d; and the group of 1.00 g/kg·bw/d had a higher cell viability of NK cells than those of the group of 0 g/kg·bw/d, and the differences were all of significance in statistics ($p<0.05$). The results of the test indicated that: the tablet of sporoderm-removed Ganoderma lucidum spore can improve the cellular immune function, the humoral immune function, the monocyte-macrophage function, and the cell viability of NK cells.

Function test for auxiliary protection against radiation hazards: the test was conducted according to the "Technical Specification for Health Food Inspection and Evaluation" (2003 edition), where mice were orally administrated for 20 days with the test doses of 3 dose groups respectively being 0.17, 0.33, and 1.00 g/kg·bw/d, and then four indicators, i.e., the number of white blood cells, the number of nucleated bone marrow cells, the SOD activity in a liver tissue, and the serum half hemolytic value ($HC_{50}$), were determined after the mice were radiated by the 60Co-γ ray once. The results showed that, the group of 1.00 g/kg·bw/d had both a higher number of white blood cells and a higher number of nucleated bone marrow cells than those of the group of 0 g/kg·bw/d on day 3 and day 14 after the radiation, and the differences were all of significance in statistics ($p<0.05$). The results of the test indicated that: the tablet of sporoderm-removed Ganoderma lucidum spore had the function of auxiliary protection against radiation hazards.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A method for preparing a tablet of sporoderm-removed Ganoderma lucidum spore powder, comprising the following steps:
    1) mixing 13-20 parts by weight of a water extract of sporoderm-disrupted Ganoderma lucidum spore powder, 3-5 parts by weight of sorbitol and 0.8-1.2 parts by weight of povidone K30 for 10-30 min, and subjecting the obtained mixture to granulating, screening and drying to obtain a granular material; and
    2) tableting the granular material obtained in step 1) to obtain the tablet of sporoderm-removed Ganoderma lucidum spore powder, wherein the water extract of sporoderm-disrupted Ganoderma lucidum spore powder is obtained by conducting water extraction, concentration, drying and pulverization on the sporoderm-disrupted Ganoderma lucidum spore powder;
    wherein the water extraction is a three-stage water extraction, wherein a temperature fora first-stage water extraction is 25-30° C., time for the first-stage water extraction is 1-3 h, and a mass of water used for the first-stage water extraction is 10-15 times larger than that of the sporoderm-disrupted Ganoderma lucidum spore powder; and temperatures for a second-stage water extraction and a third-stage water extraction are independently 95-100° C., time for the second-stage water extraction and the third-stage water extraction is independently 1-3 h, and masses of water used for the second-stage water extraction and the third-stage water extraction are independently 8-12 times larger than that of the sporoderm-disrupted Ganoderma lucidum spore powder; and
    wherein the water extract contains 2-10 g/100 g of total polysaccharides and 1.2-5 g/100 g of total triterpenes, and contains no sporoderm residues;
    wherein an amount of the water extract of sporoderm-disrupted Ganoderma lucidum spore powder, sorbitol and povidone K30 is controlled such that in the tablet of sporoderm-removed Ganoderma lucidum spore powder, a mass fraction of total polysaccharides is 1.5-7.6%, and a mass fraction of total triterpenes is 0.9-4%.

2. The method of claim 1, wherein a sieving mesh of 14-16 mesh is used during the granulation process, and a sieving mesh of 18-20 mesh is used during the screening process.

3. The method of claim 1, wherein a vacuum degree of the concentration is −0.07 to −0.09 Mpa, and the temperature of the concentration is 60-70° C.

4. The method of claim 1, wherein the drying is a microwave drying, a vacuum degree of the microwave drying is −0.08 Mpa, and a temperature of the microwave drying is 60-70° C.

* * * * *